United States Patent [19]

Pennington et al.

[11] Patent Number: 4,943,643
[45] Date of Patent: * Jul. 24, 1990

[54] MOLTEN SALT CATALYZED OXIDATION OF ALKANES OR OLEFINS USING LOWER TEMPERTURE NITRATE SALTS

[75] Inventors: B. Timothy Pennington, Sulphur; Michael C. Fullington, Lake Charles, both of La.

[73] Assignee: Olin Corporation, Cheshire, Conn.

[*] Notice: The portion of the term of this patent subsequent to Nov. 22, 2006 has been disclaimed.

[21] Appl. No.: 362,711

[22] Filed: Jun. 7, 1989

[51] Int. Cl.$^5$ .......................................... C07D 301/06
[52] U.S. Cl. ..................................... 549/532; 549/533
[58] Field of Search ................................ 549/532, 533

[56] References Cited

U.S. PATENT DOCUMENTS

| | | | |
|---|---|---|---|
| 2,530,509 | 11/1950 | Cook | 260/348.5 |
| 3,132,156 | 5/1964 | Lemon et al. | 260/348 |
| 3,647,358 | 3/1972 | Greenberg | 549/533 |
| 3,786,109 | 1/1974 | Jones | 549/533 |
| 4,785,123 | 11/1988 | Pennington | 549/532 |

*Primary Examiner*—Glennon H. Hollrah
*Assistant Examiner*—Ba K. Trinh
*Attorney, Agent, or Firm*—Dale Lynn Carlson

[57] ABSTRACT

A process for the vapor phase oxidation of olefins in molten salt catalyst to produce alkylene oxides in increased molar selectivity and per-pass yields while reducing the molar selectivity of aldehyde by-products. The process involves the use of molten nitrate salt catalyst compositions which comprise lithium nitrate and which are heated and operated at a low temperature within the range of about 180° C. up to about 250° C., more preferably 200° C. to 250° C.

11 Claims, No Drawings

MOLTEN SALT CATALYZED OXIDATION OF ALKANES OR OLEFINS USING LOWER TEMPERTURE NITRATE SALTS

This invention relates generally to alkylene oxide production and, more specifically, to an improved process involving a vapor phase reaction of olefins in molten salt compositions at low temperatures which result in increased selectivity and yield of the alkylene oxide.

Alkylene oxides (vicinal epoxy alkanes), and particularly propylene oxide, are very valuable and widely used chemicals. They have been polymerized with a wide variety of monomers to yield polymers which are useful in coating compositions and in the manufacture of molded articles. Alkylene oxides have also been reacted with alcohols to yield monoalkyl ethers which have utility as solvents in many commercial processes and which are useful as components for synthetic turboprop and turbojet lubricants.

There are many methods known in the art, for the production of alkylene oxides and, most notably, propylene oxide. One of the oldest methods is the so-called "chlorohydrin process" which involves the reaction of chlorine and water to form hypochlorous acid which is then reacted with propylene to form propylene chlorohydrin. The propylene chlorohydrin is then dehydrohalogenated to yield propylene oxide. Another method to obtain propylene oxide is by the liquid phase oxidation of propylene with organic peracids. Still another method involves the liquid phase oxidation of propylene with t-butyl hydroperoxide and/or ethylbenzene hydroperoxide.

The aforementioned known methods have serious disadvantages associated therewith. For example, the "chlorohydrin process" requires the use of chlorine which is relatively expensive and corrosive in nature, requiring special handling and expensive equipment. Additionally, the chlorohydrin saponification to propylene oxide consumes alkali chemicals such as caustic soda or lime, producing a large aqueous waste stream containing chloride salts, which require costly treatment prior to discharge from the plant. The oxidation of propylene with peracids is a potentially dangerous operation and expensive equipment is needed to guard against potentially explosive hazards when working with the peracids. Another disadvantage of this method is the high cost of peracids. The t-butyl hydroperoxide and ethylbenzene hydroperoxide processes have the disadvantages of being capital-intensive, multi-step, rather complicated processes. Furthermore, these processes require co-feedstocks of isobutane or ethylbenzene, thus constraining the practical utility of the processes for propylene oxide manufacture.

Another method which has received considerably attention in the literature is the direct oxidation of hydrocarbons with an oxygen-containing gas. This method suffers from the disadvantage that it is not specific for the production of alkylene oxides but produces a variety of other compounds including acids, esters, ethers, and oxides of carbon including carbon monoxide and carbon dioxide. The reaction does, however, possess two attributes which recommend it highly for commercial utilization, i.e., inexpensiveness of starting materials and simplicity of operation. It is primarily for these reasons that much attention in recent years has been directed to improvements in methods for the production of alkylene oxides from the direct oxidation of hydrocarbons even though the producer must necessarily contend with the concurrent production of a variety of undesired products.

By way of illustration, the prior art methods which attempted to produce propylene oxide by the oxidation of propane such as that disclosed in U.S. Pat. No. 2,530,509, assigned to Linde Air Products Company, were only partially successful. The majority of the prior art methods used conventional vertical columns and differed from each other by variations in lengths and diameter of the column, temperature, pressure, etc. However, all of these methods suffered one common disadvantage—the temperature of the reactants varied throughout the length of the column.

The temperature variations are easily explained since the oxidation reactions are exothermic and the amount of heat evolved differs with each reaction which is taking place. Thus, at various increments along the tube, conditions existed which favored the direction of the oxidation to products other than propylene oxide. These prior art methods necessitated the use of elaborate and expensive cooling apparatus.

Further developments in the art constituted attempts to maximize the desired olefin oxide production while minimizing by-product formation. For example, U.S. Pat. No. 3,132,156, assigned to Union Carbide Corporation, discloses the vapor phase oxidation of saturated aliphatic hydrocarbons to olefin oxides. The method described in the '156 patent is said to provide enhanced olefin oxide production as high as 46.2 lbs per 100 lbs of $C_3$ consumed which calculates to be about 33 percent (molar) selectivity. While this level of selectivity constituted an improvement, it remains less than might be desired from a commercial standpoint.

A molten salt process for producing alkylene oxides is disclosed in commonly-assigned Pennington U.S. Pat. No. 4,785,123 issued Nov. 15, 1988, and it is an objective of the present invention to modify the process of said Patent in order to provide a new method which substantially increases the yield or level of selectivity of alkylene oxides produced thereby.

Two major problems exist in the known molten salt oxidation processes for converting olefins such as propylene to alkylene oxides such as propylene oxide, namely the lower than desired selectivity to alkylene oxide, which is about 45%, and the larger than desired selectivity to aldehyde formation, such as acetaldehyde, which is from about 18% to 25%.

While vapor phase molten salt-catalyzed processes for oxidizing olefins to produce alkylene oxides therefrom have several advantages over known liquid phase oxidation processes, such vapor phase processes have resulted in lower selectivity to alkylene oxides and lower yields thereof than may be necessary to compete on a commercial scale with other known industrial processes. Therefore it is an objective of the present invention to provide an improved vapor phase molten salt oxidation process, the conditions of which increase the molar selectivity of the olefin to form alkylene oxide and thereby increase the yield of alkylene oxide to amounts which make the process more competitive for industrial use, while reducing the amount of low-value aldehyde by-products.

Known liquid phase processes which co-oxidize propylene and acetaldehyde require the use of large amounts of acetaldehyde, and produce large quantities of acetic acid by-product whereas the desired end-product is propylene oxide. The overall propylene oxide selectivity of such processes is not increased but acetaldehyde is converted into acetic acid, which is a more marketable material.

The present invention is based upon the discovery that the yield of alkylene oxide produced by known molten salt oxidation processes can be substantially increased by a novel process in which the composition and temperature of the molten salt composition are controlled for operation within a low, relatively narrow temperature range which has been found to favor the selectivity to alkylene oxide, whereby the selectivity to alkylene oxide is substantially increased to at least about 50% and preferably up to about 55%, and the molar selectivity to aldehydes is substantially reduced.

The present invention relates to a vapor phase process for producing an alkylene oxide comprising reacting an alkane or olefin having from 3 to 22 carbon atoms per molecule, or mixture thereof, with oxygen or an oxygen-containing gas, said alkane or olefin and said oxygen-containing gas being gaseous reactants, by contacting said gaseous reactants with a bath, stream, spray or mist of at least one molten nitrate salt catalyst containing a substantial amount of lithium nitrate, said catalyst being present in an amount sufficient to absorb any heat generated during said reaction while maintaining an essentially constant reaction temperature between about 180° C. and about 250° C. and a reaction pressure of between about 1 and about 50 atmospheres to produce an alkylene oxide in a molar selectivity of at least about 50 percent, and aldehyde by-products in a molar selectivity of less than 16 percent, based upon the amount of said olefin reactant.

It has been discovered that lower melting nitrate salt compositions comprising lithium nitrate allow smooth operation at temperatures below the melting point of the more conventional sodium nitrate-potassium nitrate salt mixtures. Lower temperature operation of the salt flow reactor has been found to lead to increased molar selectivity to alkylene oxide and to a substantially increased per-pass conversion of the olefin, i.e., a doubling of the per pass yield A further advantage of the present process is that the molar selectivity to formaldehyde and acetaldehyde, the undesirable aldehyde by-products, is substantially reduced to about one-half the amounts produced according to the aforementioned Pennington U.S. Pat. No. 4,785,123.

Several factors will affect the reactant conversion to alkylene oxide and the selectivity of alkylene oxide production vis-a-vis by-product production in accordance with the process of the present invention. For example, these factors include: the contact time of the molten salt with the oxygen-containing gas, the temperature of the reactor product gases, the molten salt temperature, the molten salt catalyst composition, the feed gas temperature, the feed gas composition, the feed gas pressure, and the co-catalyst employed (if any).

The oxygen-containing gas useful as a reactant in the present invention can be any such gas, but air preferably is employed as the oxygen-containing gas based upon its ready availability. However, other oxygen-containing gases can be employed, such as pure oxygen, and the use of oxygen is expected to be preferred in a commercial setting.

The olefin useful in the present invention can be broadly defined as an epoxidizable, olefinically-unsaturated hydrocarbon compound having from 3 to 22 carbon atoms, preferably from 3 to 15 carbon atoms, more preferably from 3 to 12 carbon atoms, most preferably from 3 to 10 carbon atoms. This definition is intended to include terminal olefins selected from the group consisting of monofunctional and difunctional olefins having the following structural formulas respectively:

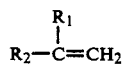

wherein $R_1$ is hydrogen or an alkyl chain, straight or branched, having 1 to 20 carbon atoms and $R_2$ is an alkyl chain, straight or branched, having 1 to 20 carbon atoms; and

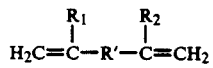

wherein $R_1$ and $R_2$ are hydrogen atoms or alkyl chains having 1 to 10 carbon atoms and R' is from 2 to 10 methylene groups. The definition also includes cyclic olefins and internal olefins The ring portions of the cyclic olefins can have up to 10 carbon atoms and one unsaturated bond and can be substituted with one or two alkyl radicals having 1 to 10 carbon atoms. The cyclic olefins are typically represented by the following structural formula:

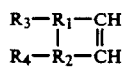

wherein $R_1$ and $R_2$ are olefin radicals having 1 to 4 carbon atoms and $R_3$ and $R_4$ represent hydrogen atoms, or one or two alkyl radicals, straight or branched chain, having 1 to 10 carbon atoms. The internal olefins are represented by the following structural formula:

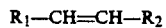

wherein $R_1$ and $R_2$ are straight chain or branched chain alkyl radicals having 1 to 10 carbon atoms.

The alkanes, olefins, and mixtures thereof, useful as reactants in accordance with the present invention generally have up to, but do not exceed, 22 carbon atoms per molecule, preferably not more than 12 carbon atoms per molecule. When a straight-chain molecule is employed, it is more preferred that such molecule not have more than ten carbon atoms When a cyclic compound is used, it is more preferred that the cyclic compound not have more than 12 carbon atoms per molecule A preferred reactant within this group is propylene.

Representative other alkylene compounds or olefins are butene-1, butene-2, isobutylene, pentene-1, hexene-1, pentene-2, cyclopentene and cycloctene. Other representative olefins are 2-methylbutene-1, 3-methylbutene-1, heptene-1, octene-1, hexene-2, hexene-3, octene-2, heptene-3, pentadecene-1, octadecene-1, dodecene-2, 2-methylpentene-2, tetramethylethylene, methylethylene, cyclobutene, cycloheptene, 2-methylheptene-1,2,4,4-trimethylpentene -1, 2-methylbutene-2, 4-methylpentene-2, 2-ethyl-3-methylbutene-1, propane, isobutane, pentane, and cyclohexane.

The alkane or olefin gas is preferably preheated to prevent condensation in the line delivering this gas to the reactor. Alternatively, both the oxygen-containing gas and the olefin gas (collectively referred to herein as "the feed gases") can be preheated to prevent condensation in any of the feed lines. However, in the absence of preheat, the molten salt will rapidly heat the feed gases up to reaction temperature. If the feed gas is preheated, it preferably is maintained at at least about 100° C. in the feed gas line(s).

The molten lithium nitrate salt(s) catalyst is maintained at a temperature between about 180° C. (356° F.) and about 250° C. (482° F.) more preferably between about 200° C. and about 250° C., most preferably between about 220° C. and about 240° C. during the reaction in accordance with the present invention.

The preferred salt compositions used according to the present invention contain from about 20 to 40 mole percent lithium nitrate and from 60 to 80 mole percent of one or more other alkali metal or alkaline earth metal nitrates. Most preferably the present salt compositions comprise mixtures of lithium, sodium and potassium nitrates containing 20–40 mole percent lithium nitrate, 40–60 mole percent potassium nitrate and 10–30 mole percent sodium nitrate.

The aforementioned temperature ranges are critical to the smooth operation of the present process and, more particularly, to producing the desired increased molar selectivity to the formation of the alkylene oxide and the beneficial reduced molar selectivity to the formation of the undesired aldehyde by-products. While it is possible to operate molten salt baths at lower or higher temperatures, including lithium nitrate salt baths as disclosed in the aforementioned Pennington U.S. Pat. No. 4,785,123, the novel and unexpected advantages of the present process have not been obtained with salt bath compositions and temperatures outside the ranges disclosed herein. In addition, it is important to maintain a sufficient isotherm across the molten salt bath so as to avoid crust formation of the salt in the bath. Such a crust formation in the salt bath can cause localized overheating of gases trapped by the crust in the bath and an associated "runaway" oxidation reaction due to overheating of the gases in the bath. In order to maintain a bath isotherm, constant stirring of the molten salt bath is preferred. Alternatively, the molten salt can be circulated by conventional means, such as the use of internal draft tubes or external pumping loops.

The ratio of alkane, olefin, or mixture thereof, to oxygen in the oxygen-containing gas in the reactor can vary over a wide range. However, in accordance with the present invention, it has been found that enhanced selectivity of alkylene oxide product is achieved by maintaining a relatively low amount of oxygen relative to the amount of alkane or olefin fed into the reactor. For example, when reacting propylene with oxygen in a molten lithium nitrate salt column at elevated pressure, a ratio of between about 2 and about 100 parts per volume of propylene per 1 part per volume of oxygen, e.g., about 1 to 35 volume percent oxygen to about 66 to 99 volume percent propylene is found to provide an enhanced selectivity of propylene oxide. A preferred ratio is between 4:1 and 30:1, most preferably between about 8:1 and 20:1. Another consideration in the selection of the amount of olefin to use as a feed is the high partial pressure of the olefin which in high concentrations can cause thermal cracking of the olefin reactant itself. Therefore, when conducting the oxidation reaction on certain olefins such as propylene at an elevated pressure, viz 75 psig, it is preferred to "cut" the amount of propylene to 50 to 75 volume percent and utilize an inert blanket (diluent") gas, such as nitrogen, to provide the remaining volume percent of feed gas. Alternatively, the diluent gas may be comprised of mixtures of oxidation by-product gases generally readily obtainable from the propylene oxide purification operations downstream of the molten salt reactor, including the aldehydes which can be recycled in order to co-oxidize them to form less objectionable by-products.

In the selection of the ratio of the volume of oxygen-containing gas relative to the volume of alkane or olefin employed in the reaction mixture, the range of ratios which might pose a flammability hazard should be avoided, as is well known. For example, when utilizing an air/propylene reactant mixture at atmospheric pressure, the range of below 7 volume percent of propylene based upon total air plus propylene should be avoided.

A co-catalyst can also be utilized in accordance with the present invention. For example, when an elemental metal, or the oxide or hydroxide thereof, is employed as a co-catalyst in conjunction with the molten salt catalyst, it is possible to lower the reaction temperature for the particular salt selected and/or enhance the selectivity or conversion to the desired olefin oxide. By way of illustration, a palladium on alumina co-catalyst or a silver co-catalyst such as silver nitrate is expected to similarly reduce the required reaction temperatures. The use of these metal co-catalysts is preferred when the reaction is conducted at atmospheric pressure. At superatmospheric pressure, an alkali metal hydroxide co-catalyst, such as sodium hydroxide, has been found to be particularly advantageous in providing enhanced selectivity to the desired product. In addition, in a continuous process employing caustic recycle, the alkali metal hydroxide is expected to enhance the desired product distribution by removing by-product carbon dioxide by forming alkali metal carbonate.

If used, the co-catalyst is generally employed in a catalytically effective amount, generally in an amount of less than about 5 (preferably between about 0.5 and about 5, more preferably in an amount between about 0.5 and about 3) weight percent based on the total amount of co-catalyst plus molten salt catalyst.

The molten salt catalyst in which the co-catalyst (if used) is suspended or dispersed, helps to maintain the co-catalyst at a constant desired temperature or isotherm. The maintenance of the co-catalyst in such an isotherm makes it possible to reduce or avoid the problems of co-catalyst de-activation that might otherwise be encountered in a non-isothermal system due to overheating of the co-catalyst itself or due to thermal degradation of product to a tarry by-product which can coat, and thus de-activate, the catalyst.

Typically, the molten salt(s) is employed in an amount on a weight basis of between about 5 times and about 100 times (preferably between about 5 times and about 50 times) the total weight of the reactants employed.

The molten salt(s), in addition to functioning as a catalyst and as an isothermal medium for the co-catalyst, if used, also serve as a temperature regulator. More specifically, the molten salt(s) have a high heat absorption capacity, enabling them to absorb large quantities of heat during the exothermic oxidation reaction while maintaining an essentially constant reaction temperature within the aforementioned critical ranges and thereby preventing a runaway reaction. The absorbed heat of reaction from this exothermic oxidation may be employed in the process of the present invention to help maintain the molten salt in a molten state and/or to heat the gaseous reactants to reaction temperatures.

One method of contacting the gaseous reactants in the presence of the molten nitrate salt is by bubbling the reactants through a bath of the molten salt. If the gaseous reactants are bubbled into the bottom of the bath or column containing the molten salt, the contact time of the reactants with the molten salt catalyst is equal to the "rise time" of the reactants through the bath or column. Thus, the contact time can be increased by increasing the length of the molten salt bath or column. An alternate method of contacting the gaseous reactants in the presence of the molten salt would be to pass the gaseous reactants through a reactor countercurrently to a spray or mist of the molten salt. This latter method is preferred since it provides for enhanced surface area contact of the reactants with the molten salt. Still another method of contacting the gaseous reactants with molten salt would be to inject the reactants into a circulating stream of molten salt, wherein the kinetic energy of both streams is utilized to provide intimate mixing through the application of nozzles, mixers, and other conventional equipment. This latter method is expected to be preferred in a commercial setting. These methods are only illustrative of types of reaction systems which may be employed in the practice of this disclosure. Other conventional methods of gas-liquid contact in reaction systems may also be employed.

The alkane, olefin or mixture thereof, feed gas(es) can be passed into the molten salt-containing reactor using a separate stream (e.g. feed tube) from the stream delivering the oxygen-containing gas to the reactor. Alternatively, the reactant gases can be fed into the reactor together in a single stream. In a preferred embodiment of the present invention, two co-axially-mounted feed gas tubes are employed. The co-axial mounting of the feed gas tubes has been found to reduce or minimize the back-up of molten salt into an unpressurized feed tube if pressure is temporarily lost in either (but not both) feed tube Mixing of the gaseous reactants prior to, or at the point of, the gas(es) inlet into the reactor is desired in order to facilitate the oxidation reaction. Mixing is suitably accomplished using an impingement mixer or sparger tube.

If a molten salt bath is used, the feed gas is preferably bubbled into the molten salt-containing reactor using a sparger. If used, the sparger is preferably positioned in the molten salt to a sparger exit port depth of between about 2 and about 1000 centimeters, preferably between about 10 and about 200 centimeters, depending upon the size of the reactor utilized and the overall depth of the molten salt in the reactor. Alternatively, the gas can be fed directly into the bottom of the reactor by a feed tube. The feed gas tubes are preferably co-axially mounted so that in the event of a loss of pressure in either gas tube, the gas in the other tube will maintain sufficient pressure to keep the molten salt from backing up into the unpressurized feed gas tube.

This process can be run in a batchwise or continuous operation, the latter being preferred. The order of introduction of the reactants is determined by the operator based on what is most safe and practical under prevalent conditions Generally, the desirability of avoiding flammable gas mixtures throughout the reaction and subsequent product separation systems will dictate the desired procedures.

The present process can be carried out by feeding a mixture of olefin, inert gas, and oxygen into a reaction vessel containing the molten lithium nitrate salt. The reaction vessel can be glass, glass-lined metal, or made of titanium. For example, a glass-lined stainless steel autoclave can be used, although, even better from a commercial point of view, is an unlined type 316 stainless steel autoclave (as defined by the American Iron and Steel Institute). A tubular reactor made of similar materials can also be used together with multi-point injection to maintain a particular ratio of reactants. Other specialized materials may be economically preferred to minimize corrosion and contamination of the molten salt and products, or to extend the useful life of the reaction system.

Some form of agitation of the molten lithium nitrate salt(s)/feed gas mixture is preferred to avoid a static system and insure the homogeneity of the molten salt, and agitation helps prevent crust formation of the salt(s) at the head gas/salt interface in the reactor This can be accomplished by using a mechanically stirred autoclave, a multi-point injection system, or a continuous process, e.g., with a loop reactor wherein the reactants are force circulated through the system. Sparging can also be used. In the subject process, it is found that increased rates of reaction are obtained by good gas-liquid contact provided by agitation of the molten salt/gas mixture.

The present process is suitably carried out at atmospheric or superatmospheric pressure Typically, the process is effected at superatmospheric pressures of up to about 100 atmospheres, preferably between about 1 atmosphere and about 50 atmospheres, more preferably between about 1 atmosphere and about 35 atmospheres. The most preferred pressure range is between about 1 and about 30 atmospheres.

It is to be understood that by-products in addition to aldehydes are also produced during the reaction. For example, some dehydrogenation of the feed is also effected, particularly at higher temperatures within the hereinabove noted temperature range, and therefore, the reaction conditions are generally controlled to minimize such production. The separation of the resulting by-products in order to recover the desired alkylene oxide product, and/or the aldehyde by-products for re-circulation, may be effected by a wide variety of well-known procedures such as: absorption in water followed by fractional distillation, absorption, and condensation. For example, the substantial amount of aldehyde by-product may be isolated by fractional distillation of the gaseous by-products and recirculated back as a gaseous reactant into the lithium nitrate catalyst. In this manner the overall yield or selectivity to alkylene oxide is further increased, which is the main objective of the present process, while the large amount of aldehyde, such as acetaldehyde, is co-oxidized and further decreased or eliminated.

The vapor phase co-oxidation reaction of the aldehydes involves the indirect oxidation of the olefin by way of the oxidation of the aldehyde to a free radical intermediate which epoxidizes the olefin to form the alkylene oxide and gaseous carbon-oxygen by-products.

The following examples are intended to illustrate, but in no way limit the scope of the present invention.

EXAMPLE 1

The salt flow reactor consists of a salt circulation loop and a gas flow through loop. The reactor section consists of $\frac{1}{4}$ inch 304 S. S. pipe 25 feet in length coiled in a three inch diameter coil and packed with static mixing elements throughout. Feed gas containing 53 volume percent propylene, 8 volume percent oxygen and 39 volume percent nitrogen at a STP flow rate of 2000 cc/min is directed at 358 psig cocurrently through the reactor section with the flowing molten salt. The reactor pressure is maintained using a back pressure regulator. The salt flow through the reactor section is 0.53 GPM of molten salt consisting of 30 mole percent lithium nitrate, 50 mole percent potassium nitrate, and 20 mole percent sodium nitrate (melting point 140 C). The cocurrent flow of molten salt and reaction gases passes through the reactor to a gas-liquid separator, which sends the salt downward to the salt circulation loop and sends the reactor off gas overhead to a condensate trap for condensible ingredients such as water and water-soluble materials such as propylene oxide and the aldehydes, the main one of which is acetaldehyde. The flowing salt is maintained at 225° degrees C. and the feed gas and salt are allowed to flow for 30 minutes, after which time the reaction is stopped by switching over to nitrogen feed gas. Analysis of reaction off gas and condensate samples by GC and GC/MS methods shows that the selectivity to propylene oxide is increased to nearly 57 percent. The per pass conversion of propylene is found to be 9.7 percent and the per pass oxygen conversion was found to be 84 percent. The product gases are analyzed for molar selectivity and determined to be:

| One Carbon Products | | Three Carbon Products | |
|---|---|---|---|
| carbon monoxide | 8.9% | propylene oxide | 56.7% |
| carbon dioxide | 13.5% | acrolein | 2.5% |
| methane | 0.02% | acetone | 1.8% |
| formaldehyde | 0.3% | allyl alcohol | 1.1% |
| methanol | 0.5% | propylene glycol | 1.5% |
| Two Carbon Products | | Four Carbons and Above | |
| ethylene | 0.04% | 1,5-hexadiene | 0.2% |
| ethane | 0.16% | 4-methyl-1,3-dioxolane | 0.2% |
| acetaldehyde | 11.7% | | |
| methyl formate | 0.3% | other | 0.2% |
| ethanol | 0.01% | | |
| methylacetate | 0.01% | | |

EXAMPLE 2

Propylene was oxidized in a similar manner as in Example 1, except that the reactor section was two feet in length. The reactor section was packed throughout with stainless steel static mixing elements as in Example 1 (the length of the reactor was variable up to about three and one half feet with feed gas injection nozzles placed at six inch intervals). Feed gas containing 70 volume percent propylene, 4 volume percent oxygen, and 26 volume percent nitrogen at a STP flowrate of 2500 cc/min was injected at 355 psig cocurrently through the reactor section with the flowing molten salt. The reactor pressure was maintained using a back pressure regulator. The salt flow through the reactor was 0.58 GPM and the composition of the salt was the same as in Example 1. The flowing salt was maintained at 233 degrees C. and the feed gas and salt were allowed to flow for one hour, after which time the reaction was stopped by switching over to nitrogen gas to blanket the reactor and the salt flow to the reactor was stopped. Analysis of the off gas and condensate samples by GC and GC/MS methods showed a 54.9% selectivity to propylene oxide, 15.9% selectivity to acetaldehyde, 20.2% combined selectivity to carbon monoxide and carbon dioxide, and the remaining 9% selectivity was divided among the 18 other products listed in Example 1. The per pass propylene conversion was 3.9% and the per pass oxygen conversion was 82 percent.

COMPARATIVE EXAMPLE 3

Propylene was oxidized in a salt flow reactor similar to that described in Examples 1 and 2, except that the salt composition was 64 mole percent sodium nitrate and 36 mole percent potassium nitrate with a melting point of about 250 degrees C. The reactor section was a six inch length of ¼ inch pipe packed with static mixer elements. Feed gas containing 36 volume percent propylene, 4 volume percent oxygen, and 60 volume percent nitrogen at a STP flowrate of 4000 cc/min was injected cocurrently through the reactor section with the flowing molten salt at 284 degrees C. The feed gas was at a feed pressure slightly above 292 psig so that it could be injected into the reactor which was maintained at 292 psig using a back pressure regulator. The feed gas and salt were allowed to flow for about one hour, after which time the reactor was shut down following procedures similar to those in Examples 1 and 2. Analysis of the reactor off gas and condensate samples showed a 46.7% selectivity to propylene oxide, 22.7% selectivity to acetaldehyde, 12.2% combined selectivity to carbon monoxide and carbon dioxide, and 18.4% selectivity divided among the 18 other products listed in Example 1. The per pass propylene conversion was 0.5% and the per pass oxygen conversion was 5.4%.

Also illustrated by Comparative Example 3, when the composition of the salt bath is modified to exclude lithium nitrate and the temperature of the bath is increased above about 250° C., the molar selectivity of propylene to propylene oxide drops substantially, i.e, by about 8 to 10%, and the molar selectivity to acetaldehyde increases substantially, i.e, by about 7 to 11%.

It is to be understood that the above described embodiments of the invention are illustrative only and that modifications throughout may occur to those skilled in the art. Accordingly, this invention is not to be regarded as limited to the embodiments disclosed herein but is to be limited as defined by the appended claims.

What is claimed is:

1. A process for producing an alkylene oxide comprising reacting an olefin having from 3 to 22 carbon atoms per molecule, or mixture thereof, with oxygen or an oxygen-containing gas, said olefin and said oxygen or oxygen-containing gas being gaseous reactants, by contacting said gaseous reactants with a bath, stream, spray or mist of at least one molten nitrate salt catalyst comprising lithium nitrate, said catalyst being present in an amount sufficient to absorb any heat generated during said reaction while maintaining an essentially constant reaction temperature, said reaction being conducted at a reaction temperature of between about 180° C. and about 250° C. and a reaction pressure of between about 1 and about 50 atmospheres to produce an alkylene oxide and a mixture of aldehyde by-products, the molar selectivity of said olefin to form said alkylene oxide being greater than about 50% and the molar selectivity of said olefin to form said aldehyde by-products being less than 16%.

2. A process according to claim 1 in which said alkylene oxide comprises propylene oxide, said olefin comprises propylene, and said aldehyde by-products comprise acetaldehyde.

3. A process according to claim in which said olefin and said oxygen-containing gas are present in a volume ratio between about 2:1 and 100:1.

4. A process according to claim 1 in which the reaction is conducted at a molten salt temperature between about 200° and 250° C. and under a pressure between about 1 and 35 atmospheres.

5. A process according to claim 4 in which the molten salt temperature is between about 220° C. and 240° C..

6. A process according to claim 1 which comprises bubbling said olefin and oxygen-containing gas reactants through a bath of said molten lithium nitrate salt catalyst.

7. A process according to claim in which the alkylene oxide and aldehyde by products produced are separated and the aldehyde by-products are recirculated back through the molten lithium nitrate catalyst.

8. A process according to claim 1 in which said molten nitrate salt catalyst comprises at least about 20 mole percent of lithium nitrate.

9. A process according to claim 8 in which said molten nitrate salt catalyst comprises about 20 to 40 mole percent lithium nitrate and from 60 to 0 mole percent of sodium and/or potassium nitrate.

10. A process according to claim in which said molten nitrate salt catalyst comprises about 20 to 40 mole percent lithium nitrate, 10 to 30 mole percent sodium nitrate and 40 to 60 mole percent potassium nitrate.

11. A process according to claim 1 for producing propylene oxide comprising reacting propylene with oxygen or an oxygen-containing gas, said propylene and said oxygen or oxygen-containing gaS being gaseous reactants. by contacting said gaseous reactants with a bath of at least one molten salt catalyst comprising lithium nitrate, said catalyst being present in an amount sufficient to absorb any heat generated during said reaction while maintaining an essentially constant reaction temperature, said reaction being conducted at a reaction temperature of between about 180° C. and about 250° C., and a reaction pressure of between about 1 and 30 atmospheres to produce propylene oxide and acetaldehyde, the molar selectivity of said propylene to form propylene oxide being greater than about 50% and the molar selectivity of said propylene to form acetaldehyde being less than 16%.

* * * * *